US009198693B2

(12) United States Patent
Rinehart et al.

(10) Patent No.: US 9,198,693 B2
(45) Date of Patent: Dec. 1, 2015

(54) MINIMALLY INVASIVE METHOD AND APPARATUS FOR STABILIZING THE SPINAL COLUMN

(71) Applicant: Spinicity, Inc., Bloomington, IN (US)

(72) Inventors: Jonathan E. Rinehart, Bloomington, IN (US); Wayne Beams, Bloomington, IN (US); Ed Morris, Bloomington, IN (US)

(73) Assignee: Innovative Surgical Designs, Inc., Bloomington, IN (US)

( * ) Notice: Subject to any disclaimer, the term of this patent is extended or adjusted under 35 U.S.C. 154(b) by 0 days.

(21) Appl. No.: 13/714,977

(22) Filed: Dec. 14, 2012

(65) Prior Publication Data
US 2013/0184759 A1    Jul. 18, 2013

Related U.S. Application Data

(60) Provisional application No. 61/570,535, filed on Dec. 14, 2011, provisional application No. 61/735,327, filed on Dec. 10, 2012, provisional application No. 61/588,823, filed on Jan. 20, 2012, provisional application No. 61/614,596, filed on Mar. 23, 2012, provisional application No. 61/614,863, filed on Mar. 23, 2012.

(51) Int. Cl.
*A61B 17/70* (2006.01)
*A61B 17/16* (2006.01)
(Continued)

(52) U.S. Cl.
CPC ......... *A61B 17/7035* (2013.01); *A61B 17/1671* (2013.01); *A61B 17/1697* (2013.01);
(Continued)

(58) Field of Classification Search
CPC ............... A61B 17/7002; A61B 17/17035; A61B 17/17037; A61B 17/7041
USPC .................. 606/264–275, 301–321
See application file for complete search history.

(56) References Cited

U.S. PATENT DOCUMENTS 4,719,905 A * 1/1988 Steffee .................. 606/262
5,304,179 A   4/1994 Wagner
(Continued)

FOREIGN PATENT DOCUMENTS

EP      122899       7/2002
EP     1252865      10/2002
WO  WO2014/006334   1/2014

OTHER PUBLICATIONS

International Search Report dated Apr. 22, 2013; International Application No. PCT/US2012/069751; International Filing Date: Dec. 14, 2012; 3 pages.
(Continued)

*Primary Examiner* — Jerry Cumberledge
(74) *Attorney, Agent, or Firm* — Blank Rome LLP (57) ABSTRACT

Implant for stabilizing a spinal column including a pedicle screw, an elongated member, and a retainer for a stabilizing rod. The elongated member can be polyaxially movably connected to the pedicle screw, and have external threads over a longitudinal periphery thereof. The retainer can be one piece, or can include an upper retainer portion and a lower retainer portion. The retainer, or the upper and lower retainer portions, can each have an opening therethrough to receive a stabilization rod to fix one implant to another. In one aspect, the upper retainer portion is internally threaded to engage external threads of the elongated member, the upper retainer portion threadably translating longitudinally along the elongated member by rotation of the elongated member about a longitudinal axis thereof. The upper retainer portion translates toward the lower retainer portion to secure and retain the rod therebetween.

20 Claims, 9 Drawing Sheets

(51) Int. Cl.
*A61B 17/88* (2006.01)
*A61B 19/02* (2006.01)
*A61B 17/00* (2006.01)
*A61B 19/00* (2006.01)

(52) U.S. Cl.
CPC .......... *A61B17/7001* (2013.01); *A61B 17/704* (2013.01); *A61B 17/7037* (2013.01); *A61B 17/7041* (2013.01); *A61B 17/7076* (2013.01); *A61B 17/7083* (2013.01); *A61B 17/7086* (2013.01); *A61B 17/8875* (2013.01); *A61B 19/026* (2013.01); *A61B 17/7011* (2013.01); *A61B 2017/0046* (2013.01); *A61B 2017/00398* (2013.01); *A61B 2017/00734* (2013.01); *A61B 2019/301* (2013.01); *A61B 2019/307* (2013.01)

(56) References Cited

U.S. PATENT DOCUMENTS

| | | | | |
|---|---|---|---|---|
| 5,591,166 | A * | 1/1997 | Bernhardt et al. | 606/266 |
| 5,800,435 | A | 9/1998 | Errico et al. | |
| 5,810,817 | A * | 9/1998 | Roussouly et al. | 606/250 |
| 6,050,997 | A * | 4/2000 | Mullane | 606/250 |
| 6,059,786 | A | 5/2000 | Jackson | 606/916 |
| 6,355,039 | B1 * | 3/2002 | Troussel et al. | 606/264 |
| 6,623,485 | B2 | 9/2003 | Doubler et al. | 606/301 |
| 7,578,833 | B2 | 8/2009 | Bray | 606/246 |
| 7,678,136 | B2 * | 3/2010 | Doubler et al. | 606/246 |
| 8,617,216 | B2 * | 12/2013 | Brumfield | 606/266 |
| 8,672,983 | B2 * | 3/2014 | Biscup et al. | 606/286 |
| 2004/0006342 | A1 * | 1/2004 | Altarac et al. | 606/61 |
| 2004/0254577 | A1 * | 12/2004 | Delecrin et al. | 606/61 |
| 2005/0038429 | A1 | 2/2005 | Elsebaie | |
| 2005/0131404 | A1 * | 6/2005 | Mazda et al. | 606/61 |
| 2005/0171537 | A1 * | 8/2005 | Mazel et al. | 606/61 |
| 2006/0052783 | A1 * | 3/2006 | Dant et al. | 606/61 |
| 2006/0167455 | A1 * | 7/2006 | Clement et al. | 606/61 |
| 2007/0149973 | A1 * | 6/2007 | Clement et al. | 606/61 |
| 2007/0161995 | A1 * | 7/2007 | Trautwein et al. | 606/61 |
| 2009/0062859 | A1 | 3/2009 | Mahoney et al. | |
| 2009/0062864 | A1 | 3/2009 | Ludwig et al. | |
| 2009/0264926 | A1 | 10/2009 | Taylor et al. | |
| 2010/0036427 | A1 * | 2/2010 | Winslow et al. | 606/264 |
| 2010/0168796 | A1 * | 7/2010 | Eliasen et al. | 606/264 |
| 2011/0245877 | A1 | 10/2011 | Pisharodi | |

OTHER PUBLICATIONS

International Preliminary Report on Patentability dated Jun. 17, 2014; International Application No. PCT/US2012/069751; International Filing Date: Dec. 14, 2012; 5 pages.
Written Opinion; International Application No. PCT/US2012/069751; International Filing Date: Dec. 14, 2012; 4 pages.
Extended European Search Report, dated Jul. 29, 2015; in corresponding European Application No. 12858327.5; 14 pages.
English translation of International Publication No. WO2014/006334.
China First Office Action; in corresponding China Application No. 201280066001.5, dated Jul. 28, 2015; 12 pages.
English translation; China First Office Action; China Application No. 201280066001.5 datd Jul. 28, 2015; 8 pages.

* cited by examiner

MINIMALLY INVASIVE METHOD AND APPARATUS FOR STABILIZING THE SPINAL COLUMN

RELATED INVENTIONS

This application claims benefit of priority of U.S. Provisional Application Nos. 61/570,535, filed Dec. 14, 2011, entitled "Minimally Invasive System and Method for Stabilizing the Spinal Column;" 61/588,823, filed Jan. 20, 2012, entitled "Disposable Kit for Minimally Invasive Spine Surgery;" 61/614,596, filed Mar. 23, 2012, entitled "Construct for Stabilization of Spinal Column;" 61/614,863, filed Mar. 23, 2012, entitled "Automatic Instrument and Kit for Spinal Surgery;" and 61/735,327, filed Dec. 10, 2012, entitled "Implants for Stabilizing the Spinal Column." All of the above-identified related applications are incorporated herein by reference.

FIELD OF THE INVENTION

The present invention relates generally to corrective spinal procedures and implants; and more particularly to a minimally invasive method, implant, and instrument system for stabilizing the spinal column.

BACKGROUND OF THE INVENTION

Spinal fusion is a surgical technique where one or more vertebrae are united to reduce movement between the vertebrae. Fusion is utilized to treat a number of spinal conditions, including spinal deformities, spinal stenosis, and spondylolisthesis. In order to maximize the likelihood of a successful fusion, instrumentation is often used as an internal splint to stabilize the vertebral column and aid in bone healing. These instrumentation systems typically utilize a screw which is inserted into the pedicle to act as an anchor. These anchors are then paired with rods to stabilize each side of the vertebral column. Many pedicle screw systems are complex, utilizing a number of instruments to anchor the screws and fix the rods in place. The instrumentation system and method described herein minimizes this complexity, reducing operating time for the end user.

Previous embodiments of this type of implant have utilized a tulip head design affixed onto a screw. In these embodiments, a stabilizing rod is inserted into the tulip head and locked into place with a locking cap. These tulip head and screw embodiments typically incorporate polyaxial movement, affording a surgeon flexibility to bend the rod to fit a specific patient's spinal anatomy.

SUMMARY OF THE INVENTION

The present invention provides a unique and novel method, implant, and instruments for stabilizing the spinal column. In one aspect, an implant of the present invention includes a pedicle screw, a retainer, and an elongated member. In this aspect, the methods, implants, and instrumentation of the present invention can be designed to allow a user to insert the implant in one piece.

In one embodiment of the invention, an implant for stabilizing a spinal column includes a pedicle screw with pedicle head at a proximal end thereof. An elongated member is fixedly connected to and extends proximally from the pedicle head, away from the pedicle screw. The elongated member has external threads over at least a portion of a longitudinal periphery thereof. Also included is a retainer having an unthreaded internal passage providing that the retainer is freely slidable over the elongated member. The retainer has an opening therethrough to receive a rod used to fix one implant to another. Lastly, a lock nut having a threaded internal passage engages the external threads of the elongated member. Threadable longitudinal translation of the lock nut distally along the elongated member, and against the retainer, secures and retains a rod between the retainer and the pedicle head, thereby providing a fixing of one implant to another.

The opening through the retainer can be configured to form a slot to receive a rod used to fix one implant to another. The slot can be longitudinally aligned within the retainer generally perpendicularly to a longitudinal axis of the implant, the slot being on one side of, and immediately adjacent to, the elongated member. In another embodiment, the retainer can include two, diametrically opposed openings therethrough, the two openings forming two diametrically opposed slots, each slot configured to receive one rod used to fix one implant to another. The two slots provide that two rod portions be secured and retained between the retainer and the pedicle head. In this another embodiment, each slot can also be longitudinally aligned generally perpendicularly to a longitudinal axis of the implant, each slot being on a diametrically opposed side of, and immediately adjacent to, the elongated member.

In a further embodiment, the elongated member includes a break-away reveal providing for shearing off of a longitudinal portion of the elongated member at a specified torsional force. The break-away reveal can be a notch in, a hole in, or a hole through the elongated member. The break-away reveal can be located on the elongated member to align the break-away reveal generally with a proximal end of the lock nut after the lock nut is translated toward the retainer to secure and retain a rod between the retainer and the pedicle head.

In an alternative embodiment, the elongated member can include reverse screw threading within a recess in a proximal end of the pedicle screw, or in a distal end of the elongated member. The distal end of the elongated member, or proximal end of pedicle screw, includes threads engageable with the respective recess. The reverse screw threading thereby allows a lock nut driver tool to provide counter torque to the implant to tighten the lock nut against a head of the pedicle screw without driving the pedicle screw further into a vertebra.

In another embodiment, the lock nut includes a recess to receive a distal tip of a lock pin during implant insertion. The lock pin can be longitudinally positioned within a drive tool, and alongside the elongated member, to prevent the lock nut from turning on, and relative to, the elongated member. This prevents the lock nut from prematurely tightening against the retainer, when the drive tool engages the implant to translate torque to the implant to drive the pedicle screw into a vertebra.

Further embodiments of the present invention provide for polyaxial movement between the elongated member and the pedicle screw. This can be achieved by a swivel ball being provided at a distal end of the elongated member or at the proximal end of the pedicle screw, with respective counter socket joint. The swivel ball and joint allows the elongated member to articulate within a head of the pedicle screw. Further embodiments may also include two piece retainers (upper and lower retainer portions). The upper and the lower retainer portions can fix and secure therebetween one or two rods. A two rod embodiment could instead be a one-piece, U-shaped rod. The U-shaped rod allows for better biomechanical balancing of the entire construct.

Accordingly, in one embodiment, an implant for stabilizing a spinal column includes a pedicle screw, and elongated member, and a retainer having an upper and a lower retainer portion. The elongated member is polyaxially movably connected to the pedicle screw, and has external threads over at least a portion of a longitudinal periphery thereof. The upper retainer portion and the lower retainer portion each have a concave opening therethrough to receive a rod used to fix one implant to another. The upper retainer portion can be internally threaded to engage the external threads of the elongated member to threadably translate longitudinally along the elongated member by rotation of the elongated member about a longitudinal axis thereof. The upper retainer portion thereby translates toward the lower retainer portion to secure and retain a rod between the upper retainer portion and the lower retainer portion to provide a fixing of one implant to another.

In another embodiment, the elongated member includes a break-away reveal providing for shearing off of a longitudinal portion of the elongated member at a specified torsional force. The break-away reveal can again be a notch in, a hole in, or a hole through the elongated member. The break-away reveal can also be located on the elongated member to align the break-away reveal generally with a proximal end of the upper retainer portion after the upper retainer portion is translated toward the lower retainer portion to secure and retain a rod therebetween.

In a further embodiment, the elongated member includes a swivel ball fixedly connected at a distal end thereof. The swivel ball resides within a concave recess of a head of the pedicle screw, thereby providing a polyaxially movable connection between the elongated member and the pedicle screw. The swivel ball can be movably secured within the concave recess of the head of the pedicle screw by a swivel connector head threadably connected, welded and/or press fit to the head of the pedicle screw. This provides the polyaxially movable connection between the elongated member and the pedicle screw. If threaded, internal threads of the swivel connector head can engage external threads of the head of the pedicle screw.

In still another embodiment, the concave openings through the upper and the lower retainer portions can form a slot to receive a rod used to fix one implant to another. The slot can be longitudinally aligned generally perpendicularly to a longitudinal axis of the implant, and the slot can be on one side of, and immediately adjacent to, the elongated member. Alternatively, the upper and the lower retainer portions each have two, diametrically opposed concave openings therethrough, forming two diametrically opposed slots, each slot being configured to receive a rod used to fix one implant to another. The two slots provide that two rod portions can be secured and retained between the upper and the lower retainer portions. If two slots, for two rods (or two rod portions), are provided, each slot can be longitudinally aligned generally perpendicularly to a longitudinal axis of the implant, each slot being on a diametrically opposed side of, and immediately adjacent to, the elongated member.

If two slots are together provided within the upper and the lower portions, for two rods (or two rod portions), the two rod portions (at the implant) could rather be one, U-shaped rod. The one, U-shaped rod can extend along a plurality of implants, with each implant securing and retaining two adjacent rod portions of the U-shaped rod. The one, U-shaped rod can have a U-shaped bend located at a respective end of the plurality of implants.

In a still further embodiment, the implant also includes a retaining pin. The retaining pin can be threadably engageable with the lower retainer portion, extending proximally, and longitudinally parallel to the elongated member. The retaining pin can pass through a through hole in the upper retainer portion.

In another embodiment, the lower retainer portion might include an unthreaded internal passage providing that the lower retainer portion is freely slidable over the elongated member. An underside of the lower retainer portion can be concave to provide for mating and tightening against an engagingly shaped head of the pedicle screw, under reduction, upon translation of the upper retainer portion toward the lower retainer portion to secure and retain a rod therebetween.

BRIEF DESCRIPTION OF THE ILLUSTRATED EMBODIMENTS

The present invention will be better understood with reference to the following description taken in combination with the drawings. For the purpose of illustration, there are shown in the drawings certain embodiments of the present invention. In the drawings, like numerals indicate like elements throughout. It should be understood, however, that the invention is not limited to the precise arrangements, dimensions, and instruments shown.

DETAILED DESCRIPTION OF THE INVENTION

Referring to FIGS. 1A-1D, an implant 1 for stabilizing a spinal column is shown. The implant 1 includes a pedicle screw 10 (a lower threaded shaft portion), a receiver/retainer 50, a threaded elongated member 40, and a lock nut 60. The elongated member 40 of the implant 1 can be seen variously to: allow the complete construct (the threaded shaft of the pedicle screw 10, the retainer 50, the elongated member 40, and the lock nut 60) to drive down into the pedicle as one unit; and to allow the elongated member 40 to apply a force to tighten the lock nut 60 to retain a rod 90 between the pedicle screw 10 and the retainer 50.

Regarding the implant 1, the lower threaded shaft portion (the pedicle screw) 10 is adapted for screwing into a vertebra. The elongated member 40 projects from a proximal end of the pedicle screw 10, in a direction opposite the pedicle screw 10, and includes an external thread. The external thread of the elongated member 40 provides threadable engagement with the lock nut 6, allowing the lock nut 6 to be tightened into place to secure the retainer 50 to a proximal head of the pedicle screw 10. Securing the retainer 50 against the proximal head of the pedicle screw 10 retains the rod 90 therebetween.

In this embodiment, the retainer 50 can be one-piece, having an unthreaded internal passage providing that the retainer be freely slidable over the elongated member. At least a portion of a distal end of the retainer 50 could be rounded, curved or concave, providing for mating and tightening against an engagingly shaped proximal end of a head of the pedicle screw, under reduction, upon translation of the retainer 50, by the locknut 60, toward the head of the pedicle screw, to secure and retain a rod 90 therebetween. The retainer 50 can have a through slot to receive a rod 90. At least a portion of the inside of the slot would be curved or rounded to mate with the rod 90 under reduction. The slot can be longitudinally aligned generally perpendicularly to a longitudinal axis of the implant, the slot being on one side of, and immediately adjacent to, the elongated member and the head of the pedicle.

The elongated member 40 can further include a break-away reveal 20 (FIG. 1B); or alternatively can include a reverse screw 30. The break-away reveal 20 or reverse screw 30 provide for the removal of portion of the elongated member 40 after insertion and spinal column stabilization. In the embodiment where the elongated member includes a break-away feature 20, the elongated member 40 can include a threaded external portion having standard threading that matches the threading of the pedicle screw 10.

During insertion of the implant 1, a lock pin 70 can be used to prevent the lock nut 60 from prematurely tightening against the retainer 50 and to transfer torque from the drive tool 95 to the pedicle screw 10 of the implant 1. The lock pin 70 can be positioned longitudinally, within the drive tool 95, alongside the elongated member 40, with distal tip thereof inserted into a recess in the lock nut 60 (see FIG. 1B). The lock pin 70, so positioned, prevents the lock nut 60 from turning on, and relative to, the elongated member 40 when the drive tool 95 engages the periphery of the lock nut 60, to translate torque to the implant 1, to drive the pedicle screw 10 into a vertebra. After insertion of the pedicle screw 10 into a vertebra, the break-away reveal 20 allows a portion of the elongated member 40 to shear away from the pedicle screw 1, under certain torque, leaving a low profile to the elongated member 40. The low profile of the sheared elongated member 40 can be a height approximating a proximal end of the lock nut 60 after the lock nut 60 is tightened to retain the rod 90 between the pedicle screw 10 and the retainer 50 (see FIG. 1B).

Figures 1A, 1C:
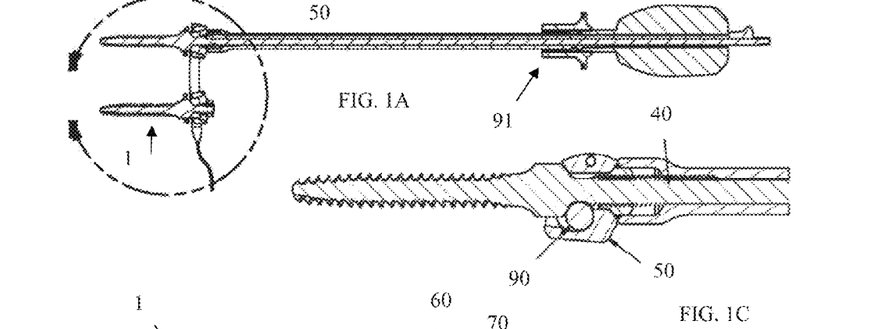
FIGS. 1A-1D illustrate in cross-section an implant and system for stabilizing a spinal column, in accordance with one embodiment of the present invention.
Figure 1B:
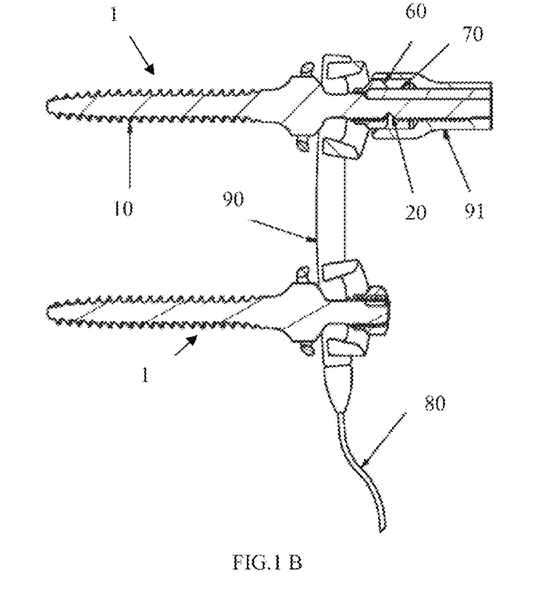
Figure 1D:
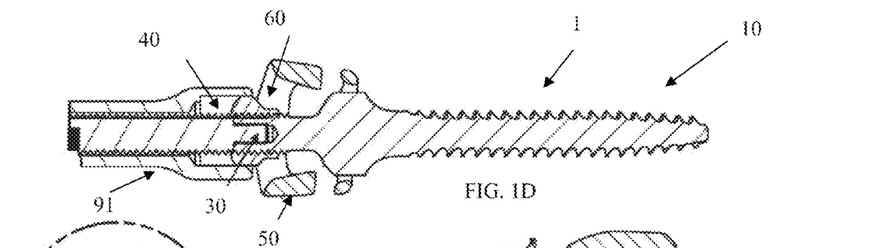

The break-away reveal 20 in the elongated member 40 can be a notch therein, or can be a hole, or a through hole. If a notch, various shapes are possible, but a V-notch if preferable. If a hole or through hole, various shapes in cross-section are possible, but an oval shaped through hole is the preferable configuration for the break-away reveal 20.

Alternatively, the elongated member 40 could include a reverse screw 30 (see FIG. 1D) rather than a break-away reveal 20. The reverse screw 30 can involve a recess in a proximal end of the pedicle screw 10, where the recess includes an internal reverse thread. A distal end of the elongated member 40 would include a mating external threaded portion for engagement within the recess of the pedicle screw 10. The internal reverse thread allows a lock nut driver tool 11 (see FIG. 2A) to provide counter torque so that the lock nut 60 can be tightened against a head of the pedicle screw 10 without driving the pedicle screw 10 further into a vertebra. Because reverse threading is utilized to tighten the lock nut 60 against the head of the pedicle screw 10, this alternative embodiment does not necessarily need to use a lock pin 70. However, a lock pin 70 may still be desired to transfer torque from the drive tool 91 to the pedicle screw 10.

Figures 2A, 2B, 2C:
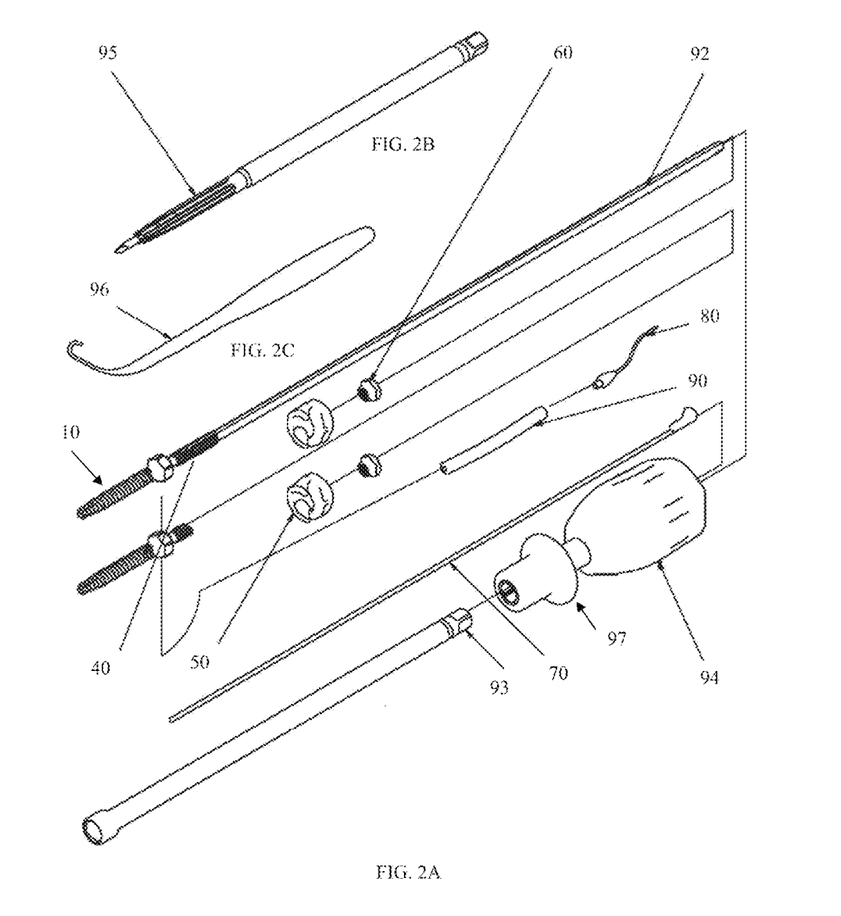
FIGS. 2A-2C illustrate (FIG. 2A in exploded view) instruments for use while performing methods of stabilizing a spinal column, in accordance with aspects of the present invention.

Referring now to FIGS. 2A-2C, the drive tool 91 includes a driver shaft 93 and a torque handle 94 with a quick release mechanism 97. The drive tool 91 (particularly the torque handle 94) provides that the implant 1 can be tightened to a finite torque specification. The quick release mechanism 97 associated with the torque handle 94 allows the torque handle 94 to be released from the driver shaft 93. The driver shaft 93 on the drive tool 91 can consist of a smooth outer member and a lower portion, where the lower portion has a recess with reverse internal thread to mate with the external thread of the elongated member 40. Depending on whether a lock pin 70 is used, the drive tool 91 may or may not require an internal cavity providing for insertion of the lock pin 70.

In another embodiment, the driver shaft 93 would be hollow, with a distal tip having an internal mechanical driver design (e.g., hex) to engage an external periphery of the head of the pedicle screw 10. An internal recess at a distal end of the quick release mechanism 97 would also have a mechanical driver design (e.g., hex, reverse threads) to engage a proximal end of the elongated member 40. The driver shaft 93 would slide over the elongated member 40, so that the distal tip thereof engages the head of the pedicle screw, then the recess at the distal end of the quick release mechanism 97 would be attached (e.g., threadably engaged) to the proximal end of the elongated member 40. In this embodiment, the driver shaft 93 has a lever arm, facilitating driving (turning of) the head of the pedicle screw by the driver shaft 93, and the torque handle facilitates driving, or turning of, the elongated member 40 to a more finite torque specification. This embodiment of the driver shaft 93 is also advantageous when using the FIGS. 3-7 embodiments of the implant of the present invention, where the elongated member 140, 240 is rotationally movable relative to the head 219 of the pedicle screw 110, 210.

After insertion of the pedicle screw 10 into a vertebra, and in order to stabilize the spinal column, a rod 90 is used to fix multiple pedicle screws 10 relative to one another. The rod 90 can consist of solid stock with a threaded outer portion on one or both ends (see FIGS. 1B and 2A). A guide cable 80 is utilized to pull the rod 90 through the retainers 50 of each implant 1. To attach the guide cable 80 to the rod 90, the rod 90 can include an inner cavity with internal threading that engages external threading on an outer portion of the guide cable 80. The guide cable 80 could alternatively attach to the rod 90 by knot or ball at end of guide cable 80 being drawn through a side hole of rod 90 and catching within an adjoining end hole of rod 90. A cable hook 96 (see FIG. 2C), which can be comprised of metal, is used to grab the guide cable 80 after the guide cable 80 has been passed through each retainer 50, to pull the guide cable 80 from a previous retainer 50 to a next retainer 50 along the spinal column.

Referring to FIG. 2B, a hybrid reamer 95, which can include a protruding, sharpened tip, can be used at the beginning of the procedure. In other pedicle screw systems, a needle pin with a sharpened tip is first inserted into a vertebra to prepare each vertebra for a reamer. A reamer tool would then be inserted to enlarge the vertebral opening, to prepare the opening for a pedicle screw. In the present invention, a needle pin and reamer are combined to form a hybrid reamer 95, used to prepare an untapped vertebra for the pedicle screw 10 in one more convenient step.

Methods of the present invention are used in the fixation of the spinal column for the treatment of a number of spinal conditions. Initially, the hybrid reamer 95 is inserted into a vertebra to prepare the pedicle thereof for insertion of the pedicle screw 10 of the implant 1. An implant 1 is inserted into pedicles on each side of a vertebra, and perhaps in a number of vertebrae, of the spinal column—each a relative distance from another. In one aspect, a drive tool 91 utilizes the threaded portion of the elongated member 40 to apply a force to drive each implant 1 into a pedicle of a vertebra. The lock pin 70 may be used to transfer a torque force from the drive tool 91 to the implant 1, to thereby prevent an inadvertent tightening of the lock nut 60 against the retainer 50 of the implant 1. In another aspect, a hollow driver shaft 93 of the drive tool 91 slides over the elongated member 40, and an internal mechanical design (e.g., hex), at a distal tip of the driver shaft 93, engages the periphery of the head of the pedicle screw (or of the lock nut 60, if using the lock pin 70) to apply a force to each implant 1 into a pedicle of the vertebra.

After inserting each pedicle screw 10 to a proper depth in each pedicle, a guide cable 80, rod 90, and cable hook 96 are used to thread the rod 90 through each retainer 50. The retainers 50 are not initially tightened down, so there exists a larger opening therein to allow for a threading of the guide cable 80 and rod 90 therethrough. After placing the guide cable 80 and the rod 90 through a first retainer 50, a cable hook 96 then grapples the guide cable 80 to pull the guide cable 80 and the rod 90 through subsequent retainers. After the rod 90 is properly placed within respective retainers 50, the guide cable 80 is detached from an end of the rod 90.

Next, if used, the lock pin 70 is disengaged from the drive tool 91. A next step of the method depends whether the elongated member 40 employs a break-away reveal 20, or a reverse screw 30. If the elongated member 40 has a break-away reveal 20, removing the lock pin 70 then allows the drive tool 91 to tighten the lock nut 60 against the retainer, to retain and secure the retainer against the head of the pedicle screw 10, thereby securing and retaining the rod 90 within the retainer 50 and against the head of the pedicle screw 10 of the implant 1. Accordingly, as the lock nut 60 is tightened, translating the lock nut 60 along the elongated member 40, the lock nut 60 pins the rod 90 against the head of the pedicle screw 10, within the retainer 50, fixing the rod 90 in place. The drive tool 91 is removed, and an instrument can then be used to shear-off a portion of the elongated member 40 at the break-away reveal 20.

If the elongated member 40 has a reverse screw 30, the lock pin 70 may or may not be used to transfer torque from the drive tool 91 to the pedicle screw 10 of the implant 1. After removing the lock pin 70, if used, a lock nut driver tool 92 is inserted into a proximal recess of the elongated member 40 (see FIG. 2A). A distal end of the elongated member 40 would include a mating external threaded portion for engagement within the recess of the pedicle screw 10. The internal reverse thread allows a lock nut driver tool 11 to provide counter torque so that the lock nut 60 can be tightened against a head of the pedicle screw 10 without driving the pedicle screw 10 further into a vertebra. Again, as the lock nut 60 is tightened, the lock nut 60 pins the rod 90 against the pedicle screw 10 and the retainer 50, fixing the rod 90 in place.

After completing the above steps, the procedure is repeated on an opposite pedicle of the vertebra, and is repeated for adjacent respective vertebrae. Upon stabilization, a biologic can be applied to aid in bone healing and to complete the procedure.

Figure 3:
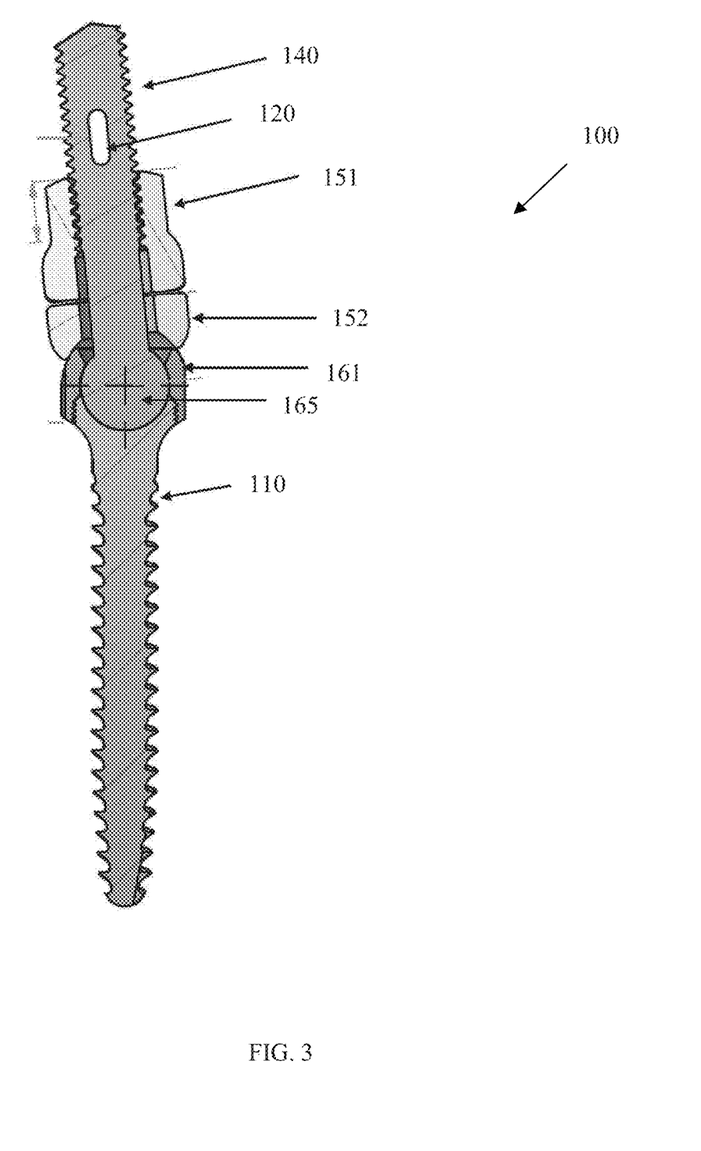
FIG. 3 illustrates in cross-section an implant for stabilizing a spinal column, in accordance with another embodiment of the present invention.

FIGS. 3-6 illustrate aspects of alternative embodiments of an implant 100 for stabilizing a spinal column. FIG. 3 illustrates a cross-section of one embodiment of the implant 100, including an externally threaded elongated member 140, a break-away reveal 120, a two-piece retainer (upper retainer 151 and lower retainer 152), a swivel connector head 161, a swivel ball 165 (in this embodiment fixedly connected at a distal end of the elongated member 140), and a pedicle screw 110. The pedicle screw 110 can be a standard pedicle screw with external threading appropriate for use in vertebral pedicles. A proximal end of the pedicle screw 110 (head of the pedicle screw 110) includes an internal recess, concave in shape, to house the swivel ball 165. The swivel ball 165 can thereby rotate freely within the head of the pedicle screw, the swivel ball 165 also allowing polyaxial movement of the elongated member 140 relative to the pedicle screw 110.

In the FIG. 3 embodiment, the externally threaded elongated member 140 includes the break-away reveal 120, allowing for shearing at a specified torque level. The break-away reveal can be positioned to align generally with a proximal end of the upper retainer 151 after tightening against the lower retainer 152 and fixation of a rod. Upon placement of the swivel ball 165 into the concave area of the head of the pedicle screw 110, a swivel connector head 161 is threaded and welded onto the head of the pedicle screw 110, so that the swivel connector head 161 movably retains in place the swivel ball 165 (and the threaded elongated member 140).

Figure 4:
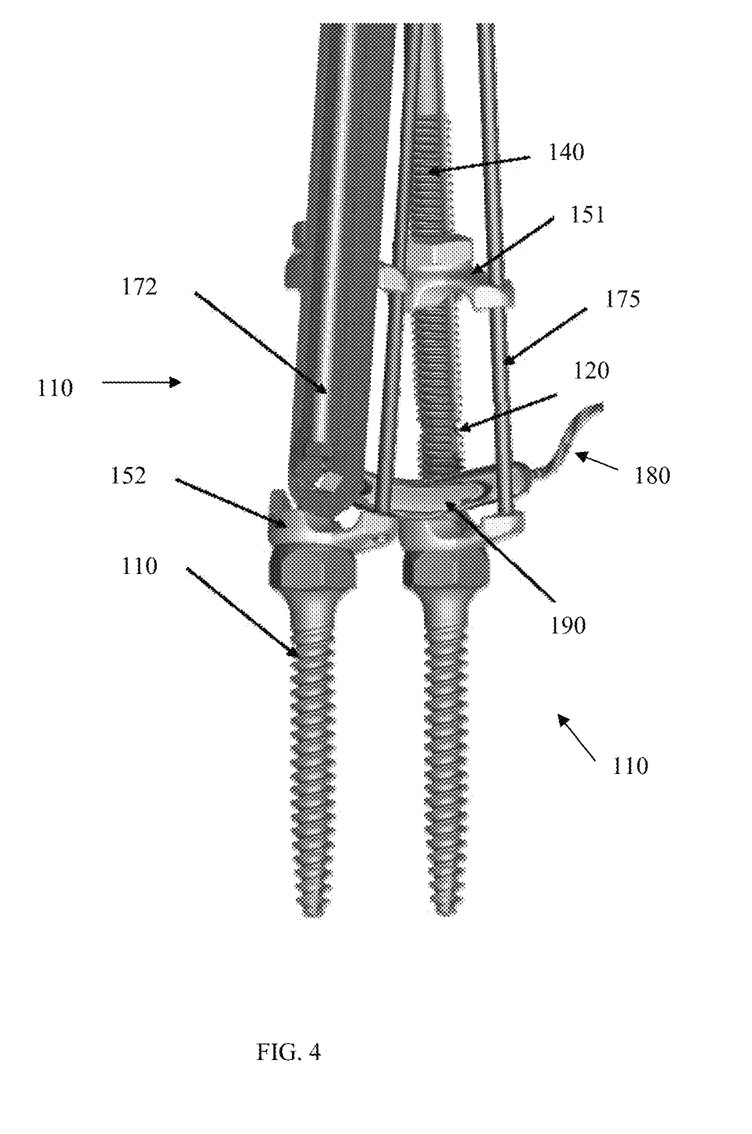
FIG. 4 illustrates in perspective view a system for stabilizing a spinal column, in accordance with another embodiment of the present invention, the system including two implants of the present invention with stabilization rod being inserted therebetween.

FIG. 4 illustrates two implant embodiments 100 for spinal stabilization, showing the implants 100 prior to vertebral insertion, rod retainment, and counter-torqueing and shearing of the elongated member 140 at the break-away reveal 120. As detailed with the FIG. 3 embodiment, a distal end of the externally threaded elongated member 140 includes the swivel ball 165, held in place within the head of the pedicle screw 110 by the swivel connector head 161. A recess within the head of the pedicle screw 110 has a concave shape (similar in shape to the swivel ball 165) so that the swivel ball 165 may rotate freely therein. This design provides the elongated member 140 with polyaxial movement and full rotation relative to the pedicle screw 110.

In this embodiment, the internally threaded upper retainer 151 can threadably translate up and down the elongated member 140 by rotation of the elongated member 140 relative to a longitudinal axis thereof (and similar rotation of the swivel ball 165 within the head of the pedicle screw 110). One advantage, in this embodiment, is that when the upper retainer 151 is threaded, on the elongated member 140, up and away from the lower retainer 152, a large area is created between the upper retainer 151, the lower retainer 152, and a retaining pin 175, for a surgeon to pass a rod 190 therethrough, with assistance, if desired, by a guide rod instrument 172.

In this embodiment, a generally concave (or possibly semicircular) slot can be included in each of the upper retainer 151 and the lower retainer 152 for placement of the rod 190. The single rod 190 is positioned, in this embodiment, generally perpendicular to the longitudinal axis of the implant 100, on one side of, and immediately adjacent to, the elongated member 140. Alternatively, the upper and the lower retainers 151, 152 can provide for placement of two rods 190 therebetween, each generally perpendicular to the longitudinal axis of the implant 100, one on each side of, and immediately adjacent to, the elongated member 140.

After the rod 190 has been passed through the area created by the elongated member 140, the upper retainer 151, the lower retainer 152, and the retaining pin 175, a surgeon can rotate the elongated member 140 to translate the upper retainer 151 toward the lower retainer 152, then securing the rod 190 between the upper retainer 152 and the lower retainer 152.

Figure 5:
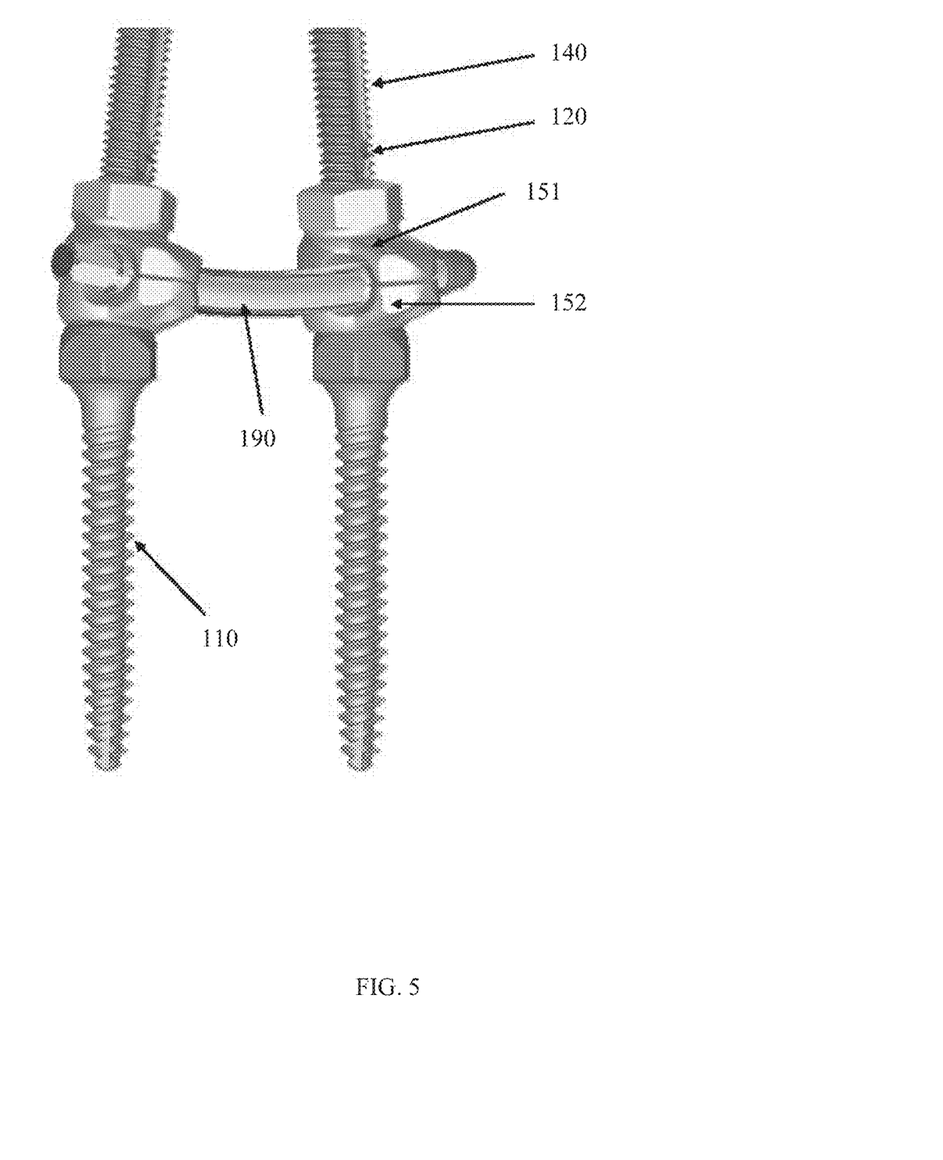
FIG. 5 illustrates in alternative perspective view the system for stabilizing a spinal column shown in FIG. 4, the system including two implants of the present invention after insertion with stabilization rod secured therebetween.

FIG. 5 generally illustrates the implants 100 of FIG. 4 in a final, rod 190 locked position (between the upper retainer 151 and the lower retainer 152), with the retaining pin 175 now removed, but prior to counter-torqueing and shear removal of a proximal portion of the elongated member 140 at the location of the break-away reveal 120. Upon completion, the implants 100 and the rods 190 provide a system to stabilize a spinal column.

Figure 6:
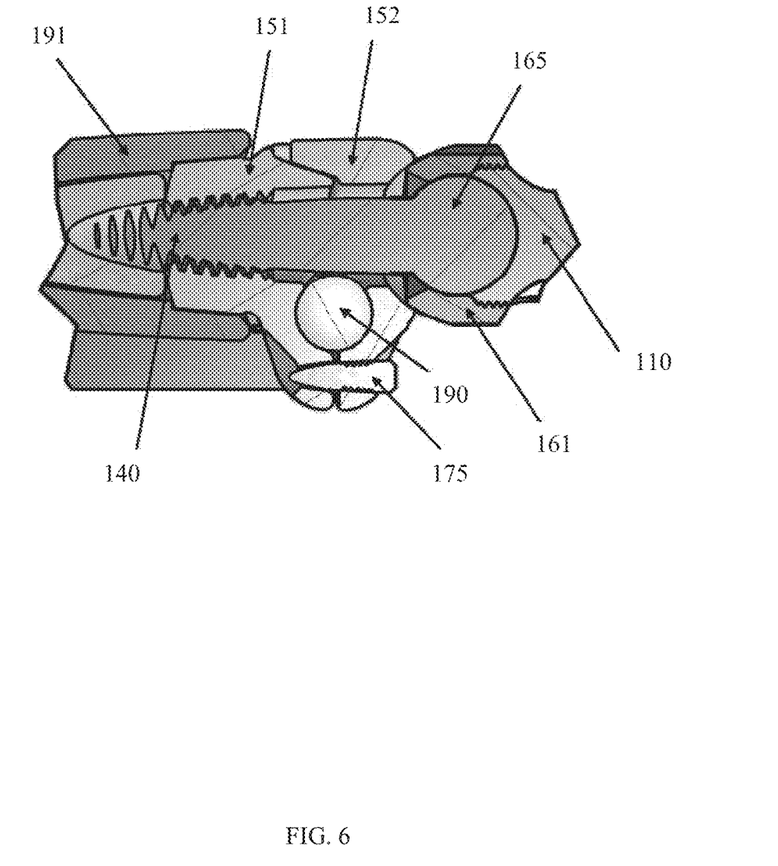
FIG. 6 illustrates in cross-section a portion of the implant for stabilizing a spinal column shown in FIG. 4.

FIG. 6 illustrates a cross-section of an implant 100 embodiment of FIG. 4, in a final, rod 190 locked position (with rod 190 retained between the upper retainer 151 and the lower retainer 152). The retaining pin 175 is inserted, and is threadably attached to the lower retainer 152. FIG. 6 also shows the swivel ball 165, located a distal end of the externally threaded elongated member 140, the swivel ball 165 held in place within the head of the pedicle screw 110 by the swivel connector head 161. As previously detailed, the recess within the head of the pedicle screw 110 has a concave shape (similar in shape to the swivel ball 165) so that the swivel ball 165 may rotate freely therein, providing the elongated member 140 with polyaxial movement and full rotation relative to the pedicle screw 110. Also shown is drive tool 191 engaging the upper retainer 151 and elongated member 140.

Figures 7A, 7B, 7C, 7D:
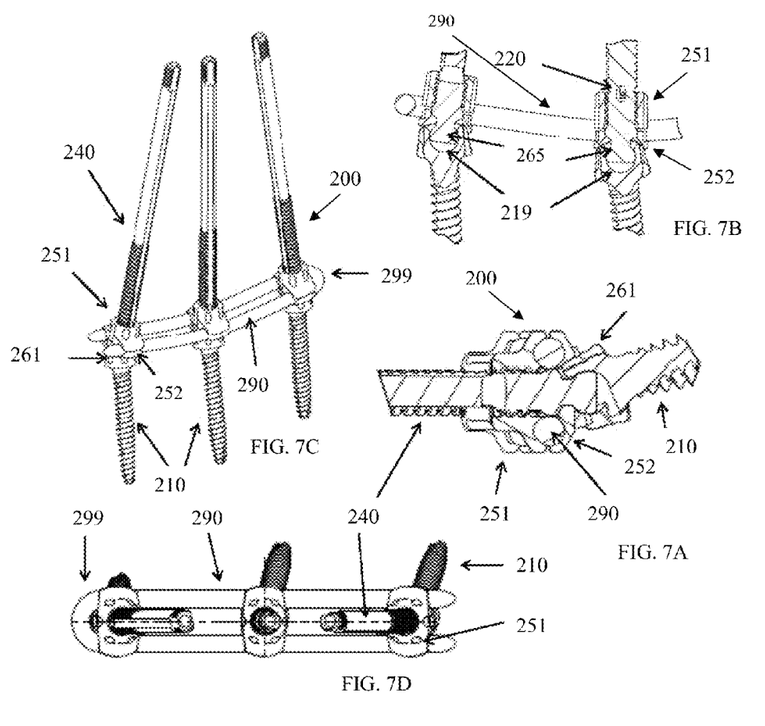
FIG. 7A-7D illustrate in cross-section an implant and system for stabilizing a spinal column, in accordance with still another embodiment of the present invention.

FIGS. 7A-7D illustrate aspects of another embodiment of an implant 200 for stabilizing a spinal column. FIG. 7A illustrates the implant 200 in cross-section, showing an externally threaded elongated member 240, a two-piece retainer (upper retainer 251 and lower retainer 252), a swivel connector head 261 (or pedicle screw cap), a swivel ball 265 (in this embodiment fixedly connected at a distal end of the elongated member 240), and a pedicle screw 210. The pedicle screw 110 can be a standard pedicle screw with external threading appropriate for use in vertebral pedicles. A proximal end of the pedicle screw 110 (head of the pedicle screw 110—or pedicle screw ball socket 219) includes an internal recess, concave in shape, to house the swivel ball 265. The swivel ball 265 can thereby rotate freely within the head of the pedicle screw (the pedicle screw ball socket 219), the swivel ball 265 also allowing polyaxial movement of the elongated member 240 relative to the pedicle screw 210.

FIG. 7B, also in cross-section, illustrates that the externally threaded elongated member 240 can also include a break-away reveal 220, allowing for shearing at a specified torsional force. The break-away reveal 220 can be positioned to align generally with a proximal end of the upper retainer 251 after tightening against the lower retainer 252 and fixation of a rod or rods 290. Upon placement of the swivel ball 265 into the pedicle screw ball socket 219, a swivel connector head (pedicle screw cap 261) is threaded and welded onto the pedicle screw ball socket 219, so that the swivel connector head 261 movably retains in place the swivel ball 265 (and the threaded elongated member 240).

As in the FIGS. 4-6 embodiment, the lower retainer 252 and the upper retainer 251 act together to tighten the rod or rods 290, and provide for fixation of the spinal column. The lower retainer 252 and the upper retainer 251 have concave cavities therein to house the rod or rods 290. The FIGS. 7A-7D embodiment of the implant 200, however, includes upper and lower retainers 251, 252 providing for placement of two rods 290 therebetween, each rod 290 being housed in a concave cavity aligned generally perpendicular to the longitudinal axis of the implant 200, one cavity on each side of, and immediately adjacent to, the elongated member 240.

As shown in FIGS. 7C-7D, although the upper retainer 251 and the lower retainer 252 are configured to retain two rods 290, adjacently inserted implants 200 may be retaining one, U-shaped rod 290, the rod having a U-shaped bend 299 at one end thereof. The concave cavities of the upper retainer 251 and the lower retainer 252 are toleranced so that, once tightened in place, the retainer 251, 252 lock the U-shaped rod 290 in place therebetween. The U-shaped rod 290 is configured to balance forces throughout the entire implant 200. The U-shaped rod 290 has bulleted tips on each of the free ends, and has a U-shaped bend 299 at a respective other end. The bulleted tips of the U-shaped rod 290 is configured for slidable insertion between the lower retainer 252 and the upper retainer 251.

In this embodiment, the lower retainer 252 can have an unthreaded internal passage so that the lower retainer 252 is able to slide freely over the elongated member 240. Additionally, the underside of the lower retainer 252 is concave providing for mating and tightening against an engagingly shaped pedicle screw cap 261 under reduction. The upper retainer 251 has a threaded internal passage to threadably engage the externally threaded elongated member 240. During tightening, the internal threads of the upper retainer 251 and the external threads of the elongated member 240 together provide reduction to tighten the lower retainer 252 and the upper retainer 251 against the U-shaped rod 290 and the top of the pedicle screw cap 261. After reduction, the upper retainer 251 is tightened further until the torsional force exceeds the sheer threshold of the break-away reveal 220 in the elongated member 240 to sheer away a portion of the elongated member 240 proximal to the break-away reveal 220.

For the FIGS. 3-7 embodiments of the implant 100, 200 of the present invention, the drive tool 91 includes a driver shaft 93 and a torque handle 94 with a quick release mechanism 97. The drive tool 91 provides that the implant 100, 200 can be tightened to a finite torque specification. The quick release mechanism 97 associated with the torque handle 94 allows the torque handle 94 to be released from the driver shaft 93. The driver shaft 93 is hollow, with a distal tip having an internal mechanical driver design (e.g., hex) to engage an external periphery of the head 219 of the pedicle screw 110, 210. An internal recess at a distal end of the quick release mechanism 97 would also have a mechanical driver design (e.g., hex, reverse threads) to engage a proximal end of the elongated member 140, 240. The hollow driver shaft 93 slides over the elongated member 140, 240, so that the distal tip thereof engages the head of the pedicle screw. Then the recess at the distal end of the quick release mechanism 97 is be attached (e.g., threadably engaged) to the proximal end of the elongated member 40. In this embodiment of the drive tool 91, the driver shaft 93 has a lever arm, facilitating driving (turning of) the head 219 of the pedicle screw 110, 210, by the driver shaft 93, and the torque handle 94 facilitates driving, or turning of, the elongated member 140, 240. Here, the torque handle 94 would rotate the elongated member 140, 240, to slidably translate the upper retainer portion 151, 251 distally toward the lower retainer portion 152, 252 to secure and fix a rod 190, 290 therebetween. As a final tightening of the upper retainer portion 151, 251 against the lower retainer portion 152, 252 another hollow driver shaft 93 can have a distal tip having an internal mechanical driver design (e.g., hex, teeth) to engage an external periphery of (or a top of) the upper retainer portion 151, 251 to specifically apply a torque thereto to fix and secure a rod 190, 290.

Figure 8A:
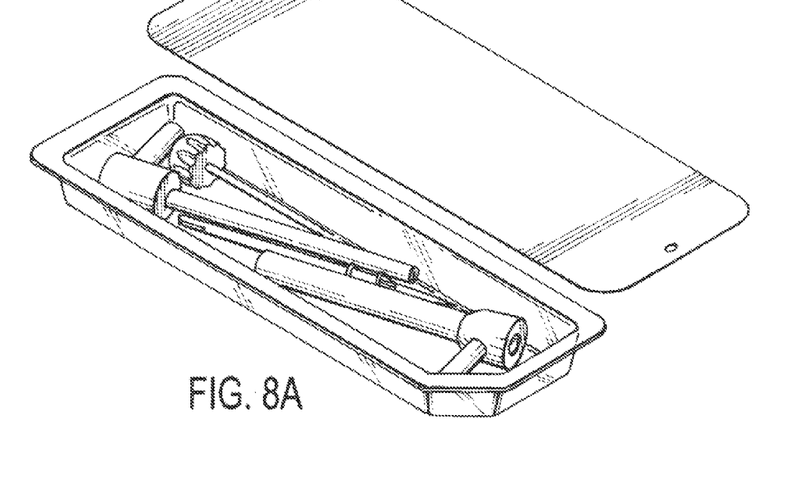
FIGS. 8A-8B illustrate a perspective view, and a side cross-section view, respectively, of a kit for housing disposable medical instruments and implants, in accordance with the present invention.
Figure 8B:
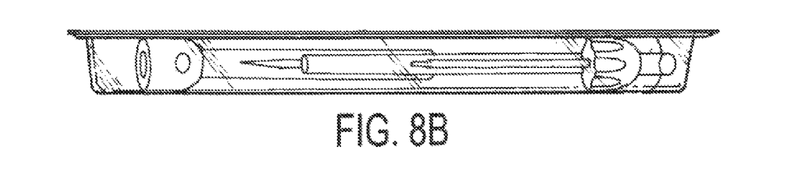

FIGS. 8A and 8B illustrate a perspective view, and a side cross-section view, respectively, of a molded polymer tray (kit) for housing disposable medical instruments and implants, along with a polymer lid for containing the instruments. The tray can be made of a polymer allowing gamma sterilization to enter into the tray, to sterilize the implants and instruments for surgical use, and to then seal the instruments and implants to prevent recontamination prior to opening and use. The kit can be molded to fit any collection of instruments and implants detailed in the present application, or any medical instruments and implants generally. While FIGS. 8A and 8B show the tray having a single, generally open cavity to house the instruments and implants, another embodiment can have custom sized and molded cavities to specifically fit each instrument and implant.

Figure 9:
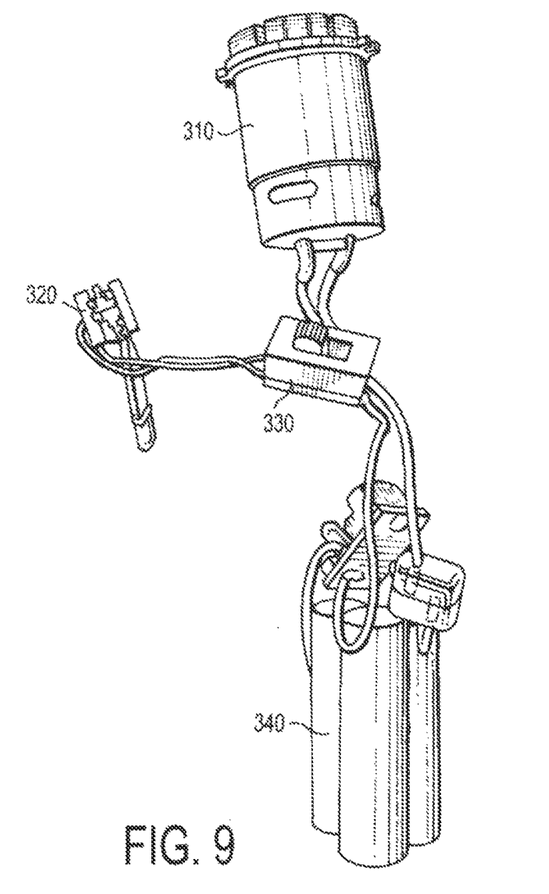
FIG. 9 illustrates an automatic instrument, and components thereof, used to drive and tighten implants and pedicle screws used in spinal surgery, in accordance with the present invention.

FIG. 9 illustrates components of an automatic instrument used in spinal surgery. The automatic instrument includes an electronic motor 310 (high torque/low torque), calibrated and geared specifically to drive and tighten implants and pedicle screws used in spinal surgery, such as the pedicle screws included in, and the implants detailed in the present invention. The motor 310 includes a switch 320 and a microprocessor 320 to control and alter gears of the motor 310. A low torque setting offers a medium-rpm, low torque drive function to tighten a retainer onto an implant of the present invention. A high torque setting offers a low-rpm, high torque drive function for shearing/breaking off a portion of an elongated member of implants of the present invention, at the break-away reveal located on the respective elongated members. The automatic instrument can further be a single-use, terminally sterilized device. A battery pack 340 can power the electronic motor 310, the switch 330, and the microprocessor 320. The automatic instrument can be packed into a kit, along with associated implants and instruments, as desired, and sterilized for single use in a sterile field.

Referring back to FIG. 3, illustrating in cross-section one implant embodiment of the present invention, provides just one example of a construct appropriate for use with the automatic instrument of FIG. 9. As detailed earlier, the implant 100 includes a threaded elongated member 140 having a break-away reveal 120, an upper retainer 151, a lower retainer 152, a swivel connector head 161, a swivel ball 165, and a pedicle screw 110. The break-away reveal 120 provides for shearing off of a portion of the elongated member 140 at a specified torque level. The automatic instrument provides that specified torque level.

Currently, almost all pedicle screws are hand tightened and torqued within the vertebra to specified limits using some type of torque-limiting handle. The polyaxial movability of certain embodiments of the present invention, such as implant 100 of FIG. 3, derived from swivel ball 165 movability within the head of the pedicle, a driving of the pedicle screw 110 into a vertebra is preferably performed using by drive tool connection generally at the head of the pedicle (or, in this embodiment, more particularly upon a periphery of the swivel connector head 165). The automatic driver of FIG. 9 can provide a tightening and torqueing function for an end user. This automatic instrument is a substantial improvement over the existing surgical instruments, which are all hand tools.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, features detailed as included in certain specific embodiments above are recognized as interchangeable and possibly included in other detailed embodiments. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:

1. An implant for stabilizing a spinal column, comprising:
   a pedicle screw;
   an elongated member polyaxially movably connected to the pedicle screw while being fully rotatable about its longitudinal axis, the elongated member having external threads over at least a portion of a longitudinal periphery thereof; and
   a two-piece retainer having a one-piece upper retainer portion and a one-piece lower retainer portion separate from the upper retainer portion, the upper and the lower retainer portions each having a central through passage along and about a respective longitudinal axis, each through passage receiving entirely therethrough the elongated member, each of the upper and the lower retainer portions also having a concave opening therethrough to receive a rod used to fix one implant to another; wherein:
   the upper retainer portion is internally threaded to engage the external threads of the elongated member, the upper retainer being threadably translatable longitudinally along the elongated member by rotation of the elongated member about its longitudinal axis; and
   the upper retainer portion being threadably translatable longitudinally along the elongated member toward the lower retainer portion to secure and retain a rod between the upper retainer portion and the lower retainer portion, thereby providing a fixing of one implant to another.

2. The implant of claim 1, wherein the elongated member further includes a break-away reveal providing for shearing off of a longitudinal portion of the elongated member, at a specified torsional force.

3. The implant of claim 2, wherein the break-away reveal is a borehole through the elongated member, the break-away reveal located on the elongated member to align the break-away reveal generally with a proximal end of the upper retainer portion after the upper retainer portion is translated toward the lower retainer portion to secure and retain a rod between the upper retainer portion and the lower retainer portion.

4. The implant of claim 1, wherein the two concave openings, one through the upper retainer portion and one through the lower retainer portion form a single, circular slot to receive a rod used to fix one implant to another, the slot being longitudinally aligned generally perpendicularly to a longitudinal axis of the elongated member, the slot being on one side of, and immediately adjacent to, the elongated member.

5. The implant of claim 1, wherein the upper and the separate lower retainer portions each include two concave openings therethrough, the four concave openings forming two diametrically opposed circular slots, each slot receiving a rod used to fix one implant to another, the two slots providing that two rod portions be secured and retained between the upper retainer portion and the lower retainer portion.

6. The implant of claim 5, wherein each slot is longitudinally aligned generally perpendicularly to a longitudinal axis of the elongated member, each slot being on a diametrically opposed side of, and immediately adjacent to, the elongated member.

7. The implant of claim 5, wherein the two rod portions form one, U-shaped rod; the one, U-shaped rod extending along a plurality of implants, each implant securing and retaining two adjacent rod portions of the U-shaped rod.

8. The implant of claim 1, wherein the central through passage of the lower retainer portion is unthreaded, providing that the lower retainer portion is freely slidable over the elongated member, and wherein a distal outer side of the lower retainer portion has a concave chamfer about a perimeter of the central through passage, the concave chamfer engagingly mating with, and tightening against, a head of the pedicle screw, under reduction, upon threadable translation, along the elongated member, of the upper retainer portion toward and against the lower retainer portion to secure and retain a rod therebetween.

9. The implant of claim 1, wherein the elongated member further includes a swivel ball fixedly connected at a distal end thereof, the swivel ball residing within a concave recess of a head of the pedicle screw, thereby providing a polyaxially movable connection between the elongated member and the pedicle screw.

10. An implant for stabilizing a spinal column, comprising:
a pedicle screw;
an elongated member polyaxially movably connected to the pedicle screw while being fully rotatable about its longitudinal axis, the elongated member having external threads over at least a portion of a longitudinal periphery thereof, and further including a swivel ball fixedly connected at a distal end thereof, the swivel ball residing within a concave recess of a head of the pedicle screw, thereby providing the polyaxially movable connection between the elongated member and the pedicle screw; and
a two-piece retainer having a one-piece upper retainer portion and a one-piece lower retainer portion separate from the upper retainer portion, the upper and the lower retainer portions each having a concave opening therethrough to receive a rod used to fix one implant to another; wherein:
the upper retainer portion is internally threaded to engage the external threads of the elongated member, the upper retainer being threadably translatable longitudinally along the elongated member by rotation of the elongated member about its longitudinal axis; and
the upper retainer portion being translatable toward the lower retainer portion to secure and retain a rod between the upper retainer portion and the lower retainer portion, thereby providing a fixing of one implant to another.

11. An implant for stabilizing a spinal column, comprising:
a pedicle screw;
an elongated member including a swivel ball fixedly connected at a distal end thereof, the swivel ball residing within a concave recess of a head of the pedicle screw, the elongated member being polyaxially movably connected to the pedicle screw while being fully rotatable about its longitudinal axis, the elongated member having external threads over at least a portion of a longitudinal periphery thereof; and
a two-piece retainer having a one-piece upper retainer portion and a one-piece lower retainer portion separate from the upper retainer portion, wherein:
the upper retainer portion is internally threaded to engage the external threads of the elongated member, the upper retainer being threadably translatable longitudinally along the elongated member by rotation of the elongated member about its longitudinal axis;
the lower retainer portion includes an unthreaded internal passage providing that the lower retainer portion is freely slidable over the elongated member, and wherein an underside of the lower retainer portion is concave providing for overlapping mating with, and tightening against, an engagingly shaped head of the pedicle screw, under reduction, upon threadable translation of the upper retainer portion toward and against the lower retainer portion to secure and retain two rod portions therebetween, thereby providing a fixing of one implant to another;
the upper and the separate lower retainer portions each including two concave openings therethrough, the four concave openings forming two diametrically opposed circular slots, each slot receiving a rod used to fix one implant to another, the two slots providing that two rod portions be secured and retained between the upper retainer portion and the lower retainer portion; and
a U-shaped rod having rounded, bulleted tip on each free end, the U-shaped rod providing that the upper and the separate lower retainer portions each secure and retain therebetween two rod portions, wherein the rounded, bulleted tips provide for slidable insertion of the U-shaped rod between a separated, spaced apart lower retainer portion and upper retainer portion, whereby the U-shaped rod provides a balance of forces when fixing one implant to another.

12. The implant of claim 11, wherein each slot is longitudinally aligned generally perpendicularly to a longitudinal axis of the elongated member, each slot being on a diametrically opposed side of, and immediately adjacent to, the elongated member.

13. The implant of claim 11, wherein the elongated member further includes a break-away reveal providing for shearing off of a longitudinal portion of the elongated member, at a specified torsional force.

14. The implant of claim 13, wherein the break-away reveal is a borehole through the elongated member, the break-away reveal located on the elongated member to align the break-away reveal generally with a proximal end of the upper retainer portion after the upper retainer portion is translated toward and tightened against the lower retainer portion to secure and retain the two rod portions between the upper retainer portion and the lower retainer portion.

15. An implant kit for stabilizing a spinal column comprising:
one or more implants, each implant according to claim 11;
a drive tool instrument providing for insertion and tightening of the one or more implants to a finite torque specification; and
a polymer tray allowing for packaging and sterilization of the one or more implants, and of the drive tool instrument.

16. The implant kit of claim 15, wherein the tray is molded to provide individual fit for each of the one or more implants, and of the drive tool instrument.

17. The implant kit of claim 15, further comprising a hybrid reamer, a cable hook, a guide cable, and a rod.

18. The implant kit of claim 15, wherein the drive tool includes a driver shaft and a torque handle with a quick release mechanism.

19. An implant for stabilizing a spinal column, comprising:
a pedicle screw;
an elongated member polyaxially movably connected to the pedicle screw while being fully rotatable about its longitudinal axis, the elongated member having external threads over at least a portion of a longitudinal periphery thereof; and
a two-piece retainer having a one-piece upper retainer portion and a one-piece lower retainer portion separate from the upper retainer portion, the upper and the lower retainer portions each having a concave opening therethrough to receive a rod used to fix one implant to another; wherein:
   the upper retainer portion is internally threaded to engage the external threads of the elongated member, the upper retainer being threadably translatable longitudinally along the elongated member by rotation of the elongated member about its longitudinal axis;
   the upper retainer portion being translatable toward the lower retainer portion to secure and retain a rod between the upper retainer portion and the lower retainer portion, thereby providing a fixing of one implant to another; and
   the lower retainer portion includes an unthreaded through passage, providing that the lower retainer portion is freely slidable over the elongated member, and wherein a distal outer side of the lower retainer portion has a concave chamfer about a perimeter of the through passage, the concave chamfer engagingly mating with, and tightening against, a head of the pedicle screw, under reduction, upon threadable translation, on the elongated member, of the upper retainer portion against the lower retainer portion to secure and retain a rod therebetween.

20. An implant kit for stabilizing a spinal column comprising:
one or more implants, each implant according to claim 1, or claim 4, or claim 19;
a drive tool instrument providing for insertion and tightening of the one or more implants to a finite torque specification; and
a tray allowing for packaging and sterilization of the one or more implants, and of the drive tool instrument.

\* \* \* \* \*